United States Patent [19]

Vreugdenhil et al.

[11] Patent Number: 5,321,161

[45] Date of Patent: Jun. 14, 1994

[54] HYDROGENATION OF NITRILES BY A TUNGSTEN CARBIDE CATALYST

[75] Inventors: Willem Vreugdenhil, Katonah; Fawzy G. Sherif, Stony Point; Johst H. Burk, Mohegan Lake, all of N.Y.; James F. Gadberry, Danbury, Conn.

[73] Assignee: Akzo nv, Arnhem, Netherlands

[21] Appl. No.: 62,673

[22] Filed: May 17, 1993

[51] Int. Cl.$^5$ ............................................. C07C 209/48
[52] U.S. Cl. ..................................... 564/490; 502/177; 564/493
[58] Field of Search ................. 564/490, 493; 502/177

[56] References Cited

U.S. PATENT DOCUMENTS

| | | | |
|---|---|---|---|
| 3,696,153 | 10/1972 | Kershaw et al. | 260/583 K |
| 4,375,003 | 2/1983 | Allain et al. | 564/492 |
| 4,552,862 | 11/1985 | Larkin | 502/306 |
| 4,845,298 | 7/1989 | Inagaki et al. | 564/490 |
| 5,130,491 | 7/1992 | Zimmerman | 564/490 |
| 5,200,060 | 4/1993 | Sajkowski et al. | 208/108 |

OTHER PUBLICATIONS

J. Chem. Society, Perkin II (1973), pp. 1400–1402.
J. Chem. Phys. 88(6), Mar. 15, 1988, pp. 4037–4045.
J. Phys. Chem. 1988, 92, 6694–6700.
J. Phys. Chem. 1989, 93, 5859–5865.

Primary Examiner—Richard L. Raymond
Assistant Examiner—Scott C. Rand
Attorney, Agent, or Firm—Richard P. Fennelly; Louis A. Morris

[57] ABSTRACT

Nitriles can be hydrogenated to amines by heating the nitrile in the presence of hydrogen and a tungsten carbide catalyst, such as are formed by the calcination of a tungsten salt with an acyclic compound containing-nitrogen-hydrogen bonding.

8 Claims, No Drawings

HYDROGENATION OF NITRILES BY A TUNGSTEN CARBIDE CATALYST

BACKGROUND OF THE INVENTION

The hydrogenation of nitriles has been taught using a number of transition metal catalysts such as those of cobalt or nickel (see U.S. Pat. Nos. 4,375,003; 4,552,862; 4,845,298; 5,075,506; and 5,130,491). The use of a catalyst derived from an iron compound in the catalytic hydrogenation of adiponitrile is taught in U.S. Pat. No. 3,696,153.

The use of molybdenum nitride in the temperature programmed reduction or hydrogenation of acetonitrile has been reported by G. W. Haddix et al., in Journal of Physical Chemistry 1989, 93, 5859–5865.

G. Vertes et al. and coworkers reported in Journal of the Chemical Society, Perkin, II, 1973, pp. 1400–1402, the selective catalytic behavior of tungsten carbide in the liquid-phase hydrogenation of aromatic nitro-, and nitroso-compounds as well as for aliphatic nitro-compounds and for quinones.

Two quite recent disclosures regarding what is termed "evidence for nitrile hydrogenation" on $W(100)-(5\times 1)-C$ is provided by J. G. Serafin and C. M. Friend in Journal of Physical Chemistry 1988, 92, 6694–6700, and Journal of Chemical Physics 88(6), Mar. 15, 1988, 4037–4045. In these publications the $W(100)-(5\times 1)-C$ surface was chosen as a model tungsten carbide surface. While these workers described N—H bond formation on absorbed acetonitrile, which is referred to as "nitrile hydrogenation" the actual species formed was $CH_2CNH$, rather than $CH_3CNH$ or $CH_3CNH_2$, thereby demonstrating that the actual reaction was a 1,3 hydrogen shift reaction rather than an actual reduction or hydrogenation. While these papers demonstrate that tungsten carbide can activate nitriles for a 1,3 hydrogen shift reaction they do not teach the actual reduction of nitriles to amines on tungsten carbide. They also do not show the formation and recovery of primary, secondary or tertiary amines. These papers also show formation of an intermediate isomer to acetonitrile, namely $CH_2CNH$ at temperatures of 190° to 400° K, with its partial decomposition to acetonitrile above 400° K, and partially to carbon, nitrogen, and hydrogen at 700° K.

SUMMARY OF THE INVENTION

In its broadest context the present invention relates to the hydrogenation of a nitrile to an amine using a tungsten carbide catalyst.

DESCRIPTION OF PREFERRED EMBODIMENTS

The tungsten carbides which may be used in the process of the present invention can be formed by the calcination of a mixture of a non-oxygen-containing acyclic compound containing carbon-nitrogen-hydrogen bonding and a tungsten salt as covered in U.S. Ser. No. 878,726, filed May 4, 1992, which is incorporated herein by reference. The terminology "acyclic compound containing carbon-nitrogen-hydrogen bonding" is intended to cover non-cyclic compounds which are essentially free of oxygen and which have covalent bonds between carbon and nitrogen and between nitrogen and hydrogen. Preferably, the compounds useful include: guanidine, the deammoniated derivatives of guanidine (e.g., cyanamide, dicyandiamide or dicyanimide), the adducts (e.g., hydrochlorides or carbonates) of guanidine, or the adducts of the deammoniated derivatives of guanidine. The compounds which can be used include guanidine, its deammoniated derivative cyanamide, and the deammoniated derivative of cyanamide which is dicyanimide. Another compound that can be used is the deammoniated derivative of guanidine and cyanamide which is termed dicyandiamide or cyanoguanidine. These compounds can be used as such or can be used in the form of adducts, such as their hydrochlorides or carbonates.

All of these compounds are free of oxygen and contain at least one carbon to nitrogen to hydrogen covalent bond.

The foregoing types of acyclic compounds are mixed with an appropriate tungsten salt prior to being calcined in accordance with the present invention. The type of metal salt which is preferred is a halide such as a chloride. The tungsten salt and acyclic compound are mixed preferably in approximate stoichiometric amount for the final tungsten carbide which is desired. Mixing can be achieved by adding solvents of each component or by admixing the solid dry components. The reaction, in the case of use of the guanidine hydrochloride as a reagent, may be represented by the following equation:

$$3\ \text{GuanidineHCl} + WCl_6 \rightarrow WC + HCl + NH_2Cl$$

The above equation only presents the major products of the reaction. Other intermediates such as chlorine gas and cyanide may also be formed in addition to chloramines ($NH_2Cl$ and $NHCl_2$).

The calcination needs to be conducted at temperatures sufficiently high, e.g. from about 400° C. to about 900° C. for a sufficiently long length of time, e.g. for about one hour to about five hours under an appropriate inert atmosphere such as helium, argon or nitrogen. The tungsten carbide formed is considered to be an interstitial alloy and is an excellent electrical conductor having a metallic color and good hydrolytic stability. The tungsten carbide product can also be an excellent catalyst for a number of reactions normally carried out by the more expensive noble metals. Thus far, most tungsten carbides prepared by other processes have surface areas between 30 and 100 m²/g. For example, tungsten carbide prepared from tungsten trioxide, methane, and hydrogen, according to the process described by E. Iglesia et al., Journal of Catalysis, 131, 523 (1991), has a surface area of about 30 m²/g.

The resulting tungsten carbide product according to the present invention has been found to be a high purity tungsten carbide of high porosity and high surface area, for instance as surface area of over 120 m²/g, preferably 200–300 m²/g.

The resulting tungsten carbide has a low carbon content, e.g. below about 10% by weight.

The same bulk tungsten carbides could be supported on an inert material for the purpose of reducing cost and effective handling of extrudates of the mixtures. The inert material can be one such as silica, alumina, titania, zirconia, and mixtures thereof. The inert materials can be precalcined at the temperatures previously described to remove trace moisture and air inside their pores. These inert materials can then be mixed with the solid reactants (i.e., transition metal salt and acyclic compound containing C—N—H bonding) and calcined as such or after being formed into tablets or extrudates to yield the desired supported tungsten carbide compositions.

The hydrogenation of the nitriles, which can be of the general formula RCN where R is alkyl of from about 1 to about 18 atoms, to form amines of the structure $RCH_2NH_2$, can be easily achieved by heating the nitrile over the afore mentioned tungsten carbide catalyst in the presence of hydrogen at elevated temperatures of from about 90° C. to about 500° C.

The foregoing invention is further understood by the Examples which follow.

EXAMPLE 1

A tungsten carbide catalyst was prepared by mixing 12 g $WCl_6$ of tungsten hexachloride (0.03 mole) with 8.6 g of guanidine hydrochloride $HN=C-(NH_2)_2HCl$, 0.09 mole, (from Aldrich Chemicals) followed by heating the mixture from room temperature to 200° C. in two hours, holding at 200° C. for two hours, then raising the temperature to 750° C. in seven and one-half hours, and holding it at 750° C. for two hours under nitrogen. The powder that was formed weighed 5.5 g. X-ray diffraction analysis showed it to be tungsten carbide ($W_6C_{2.54}$). Its surface area was 122 m²/g.

EXAMPLE 2

This Example illustrates the hydrogenation of nitriles to amines using a tungsten carbide catalyst derived from guanidine.

Hydrogen (10 ml/min) was passed through a saturator filled with propionitrile at 24° C., and the mixture was passed over the tungsten carbide catalyst at 150°–300° C. The catalyst that was prepared in Example 1 had been pretreated at 550° C. with hydrogen for fifteen hours. A mixture of propylamine, dipropylamine and tripropylamine was formed in the reactor, according to GC analysis. At temperatures above 250° C. formation of propane was also observed.

Changing the flow rate and the hydrogen to propionitrile ratio affects the product mix in the conversion of propionitrile at various temperatures:

| Temp. (°C.) | % Conv. | Product Distribution (%) | | |
|---|---|---|---|---|
| | | Propane | Propyl-amine | Dipropyl-amine | Tripropyl-amine |
| 150 | None | 0 | 0 | 0 | 0 |
| 185 | 35 | <1 | 9 | 90 | 0 |
| 230 | 90 | 3 | 10 | 63 | 24 |

EXAMPLE 3

This Example describes the preparation of the catalyst which was used in Example 4, below.

A precursor solution was prepared by first dissolving 8.6 g of guanidine hydrochloride, 0.09 mole, in 75 cc absolute ethanol, then adding slowly 12 g $WCl_6$, 0.03 mole, over ten minutes with intermittent cooling of the solution until all $WCl_6$ had dissolved. The resulting solution was brown. This solution was then added slowly to a selected zeolite (1/16" extrudates, Type 5A molecular sieve from Fisher with an effective pore size of 5 Å) that had been precalcined under $N_2$ at 750° C. for seven and one-half hours. Then, 37.5 cc of the solution was added to 35 g of this zeolite. This gave a wet product that was dried under $N_2$ and then calcined to 750° C. over seven and one half hours and held at 750° C. for two hours, also under $N_2$. This catalyst is referred to as "Catalyst A".

In the second experiment, 37.5 cc of the solution of the precursor was added to 28 g of another zeolite, 1/16" extrudates, Type RI 8687 from Akzo Chemicals. This catalyst comprised 80% of zeolite Y and 20% of alumina, had an effective pore size of 7 Å, had a surface area of 649 m²/g, and had a silica content of 64.6% by weight and an alumina content of 33.8% by weight. The wet extrudates were treated as described above. The final catalyst is referred to as "Catalyst B".

EXAMPLE 4

This Example is analogous to Example 2, above, and illustrates the conversion of acetonitrile to ethylamine using Catalyst B from Example 3, above, with acetonitrile, rather than propionate. Hydrogen gas was passed over five grams of the catalyst that had been preactivated with hydrogen at 500° C. for sixteen hours prior to testing. The results were as follows:

| Temp. (°C.) | % Conv. of Acetonitrile | % Product Distribution | | |
|---|---|---|---|---|
| | | Ethylamine | Diethylamine | Hydro-carbons |
| 200 | 0 | 0 | 0 | 0 |
| 300 | 71 | 72.4 | 0 | 9.1 |
| 338 | 93.6 | 77.1 | 1.1 | 5.9 |
| 384 | 98.2 | 76.4 | 1.1 | 7.3 |
| 435 | 97.5 | 29.2 | 4.8 | 46.0 |

It is clear that the optimum hydrogenation of acetonitrile to the desired product, ethylamine, was between 300° C. and 384° C. under the test parameters employed.

EXAMPLE 5

A tungsten carbide catalyst was prepared as described in Example 1 with the exception that guanidine carbonate was used rather than guanidine hydrochloride. Upon activation with hydrogen at 550° C. for sixteen hours, using a hydrogen flow of 10 cc/min, the product was tested for the hydrogenation of thiazole.

The apparatus used in this Example to test the hydrogenation activity involved use of hydrogen gas from a cylinder which was passed at room temperature (24°–25° C.) through a reservoir of thiazole which was dissolved in xylenes (v/v ratio of thiazole/xylene: 2/8). The saturated hydrogen gas was then introduced into a 5 cc reactor tube, heated to the desired reaction temperature, and containing 0.5 g of catalyst supported on glass wool in the middle portion of the tube reactor. Gaseous products were analyzed on stream using a gas chromatograph.

The following catalytic activity and selectivity data were obtained:

| Catalyst Temperature (°C.) | & Conversion | % Selectivity to Thiazolidine |
|---|---|---|
| 110 | 9.5 | 6 |
| 136 | 10 | 10 |
| 160 | 20 | 30 |

This Example shows that sulfur and nitrogen-containing compounds can be hydrogenated without poisoning of the catalyst used in this Example.

The foregoing Examples should not be construed in a limiting sense since they are intended to merely set forth certain preferred embodiments of the present invention.

The claims which follow set forth the scope of protection sought.

We claim:

1. A process for the hydrogenation of a nitrile to an amine which comprises heating the nitrile in the presence of hydrogen and a tungsten carbide catalyst.

2. A process as claimed in claim 1 wherein the tungsten carbide catalyst is formed by the calcination of a tungsten salt in the presence of an acyclic compound containing carbon-nitrogen hydrogen bonding.

3. A process as claimed in claim 2 wherein the acyclic compound is selected from the group consisting of guanidine, cyanamide, dicyanimide, dicyandiamide, and the hydrochloride or carbonate adducts thereof.

4. A process as claimed in claim 2 wherein the acyclic compound is selected from the group consisting of guanidine and the hydrochloride or carbonate adducts thereof.

5. A process as claimed in claim 1 wherein the catalyst is supported on an inert material.

6. A process as claimed in claim 2 wherein the catalyst is supported on an inert material.

7. A process as claimed in claim 3 wherein the catalyst is supported on an inert material.

8. A process as claimed in claim 4 wherein the catalyst is supported on an inert material.

* * * * *